US00PP32221P3

(12) United States Plant Patent
Martinelli et al.

(10) Patent No.: US PP32,221 P3
(45) Date of Patent: Sep. 22, 2020

(54) STRAWBERRY PLANT NAMED 'CIVRH612'

(50) Latin Name: ***Fragaria* x *ananassa***
Varietal Denomination: CIVRH612

(71) Applicant: C.I.V.—CONSORZIO ITALIANO VIVAISTI—SOCIETÀ CONSORTILE A R.L., Comacchio FE (IT)

(72) Inventors: Alessio Martinelli, Ferrara (IT); Michelangelo Leis, Ferrara (IT)

(73) Assignee: C.I.V.—CONSORZIO ITALIANO VIVAISTI—SOCIETÀ CONSORTILE A R.L., Comacchio (IT)

( * ) Notice: Subject to any disclaimer, the term of this patent is extended or adjusted under 35 U.S.C. 154(b) by 0 days.

(21) Appl. No.: 16/602,447

(22) Filed: Oct. 8, 2019

(65) Prior Publication Data

US 2020/0120843 P1 Apr. 16, 2020

(30) Foreign Application Priority Data

Oct. 10, 2018 (QZ) ..... PBR 2018/2554

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209
CPC ..... A01H 5/08; A01H 6/74
See application file for complete search history.

*Primary Examiner* — Annette H Para
(74) *Attorney, Agent, or Firm* — Foley & Lardner LLP

(57) ABSTRACT

This invention relates to a new and distinct variety of strawberry plant named 'CIVRH612'. This new everbearer strawberry plant named 'CIVRH612' is primarily adapted to the climate and growing conditions of the high chill areas. It is characterized by a rustic plant which is quite tolerant to leaf and root diseases and slightly susceptible to mildew. The plant has medium vigor, upright habit and good productivity also in the second year of growing. The fruit has a bright red color, conical shape, good size constant throughout the picking season and excellent skin resistance. The picking season is wide and constant. 'CIVRH612' has excellent organoleptic characteristics with aromatic notes of wild strawberry. The flavor is juicy and sweet with high brix levels. Stalk removal is very easy and the fruit is suitable for fruit salads. The fruit has a very good shelf life.

4 Drawing Sheets

Latin name of the genus and species of the plant claimed: *Fragaria* x *ananassa.*

Variety denomination: 'CIVRH612'.

BACKGROUND OF THE INVENTION

The present invention relates to a new and distinct strawberry variety named 'CIVRH612'.

The new strawberry 'CIVRH612' is a product of a planned breeding program conducted by the inventor(s), Leis Michelangelo and Martinelli Alessio, in San Giuseppe di Comacchio (Ferrara), Italy. The objective of the breeding program is to develop new everbearer strawberry varieties with high chill requirement, good productivity also in the second year (two-years production) and excellent shelf life. Select early varieties with a wide harvest period with excellent organoleptic characteristics and skin resistance.

This new strawberry 'CIVRH612' is a result of a controlled cross made by the inventors in 2011, in San Giuseppe di Comacchio (Ferrara), Italy. The female or seed parent is the not released selection of Consorzio Italiano Vivaisti named 3H1F-11. The male or pollen parent is the not released selection of Consorzio Italiano Vivaisti named S7V9-9.

The new strawberry 'CIVRH612' was discovered and selected by the inventors as a single flowering plant within the progeny of the stated cross in 2013 in San Giuseppe di Comacchio (Ferrara), Italy. This propagation has demonstrated that the combination of characteristics as herein disclosed for the new cultivar are firmly fixed and retained through successive generations of asexual reproduction. The new cultivar reproduces true to type.

After its selection, the new variety was asexually propagated by stolons in a nursery located in San Giuseppe di Comacchio (Ferrara), Italy. The new variety was tested over the next several years at Consorzio Italiano Vivaisti San Giuseppe di Comacchio (Ferrara), Italy and in different European areas with high chill conditions.

BRIEF SUMMARY OF THE INVENTION

'CIVRH612' is an everbearer variety with high chill requirement.

The following traits have been repeatedly observed and are determined to be unique characteristics of 'CIVRH612', which in combination distinguish this strawberry plant as a new and distinct variety:

1. everbearer variety with high chill requirement;
2. good productivity also in the second year of growing;
3. good fruit size constant throughout the picking season;
4. very sweet fruit with excellent aromatic notes of wild strawberry;
5. excellent shelf life; and
6. early and wide harvest during the season.

Of the many commercial cultivars known to the present inventor, the most similar in comparison to the new strawberry variety 'CIVRH612' is the patented variety of Consorzio Italiano Vivaisti named Murano. Plants of the new strawberry variety 'CIVRH612' differ from plants of strawberry variety 'Murano' in the characteristics described in Table 2:

TABLE 2

| Characteristic | 'CIVRH612' | 'MURANO' |
|---|---|---|
| Fruit: attitude of sepal | Downwards | Outwards |
| Fruit: difference in shape of terminal and other fruit | Moderate | Slight to moderate |
| Fruit: shape | Ovoid | Conical |

BRIEF DESCRIPTIONS OF THE PHOTOGRAPHS

The accompanying color photographs illustrate the overall appearance of typical specimens of the new strawberry variety 'CIVRH612', at various stages of development as true as it is reasonably possible with color reproductions of this type. Color in the photographs may differ slightly from the color values cited in the botanical description which accurately describe the color of 'CIVRH612'. The depicted plant and plant parts of the new strawberry variety 'CIVRH612' were taken in San Giuseppe di Comacchio (Ferrara), Italy, and are approximately 3 to 5 months old.

DETAILED BOTANICAL DESCRIPTION

Figure 1:
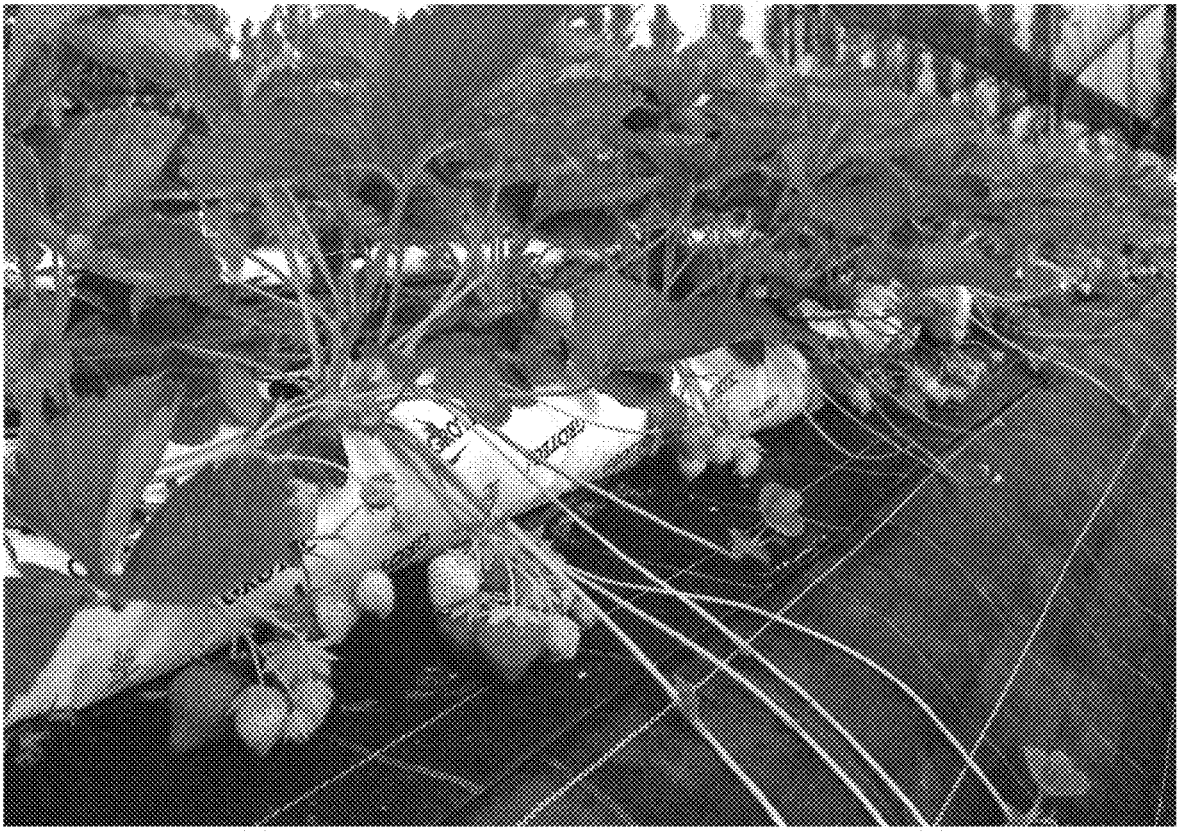
FIG. 1 shows typical plants of 'CIVRH612'.
Figure 2:
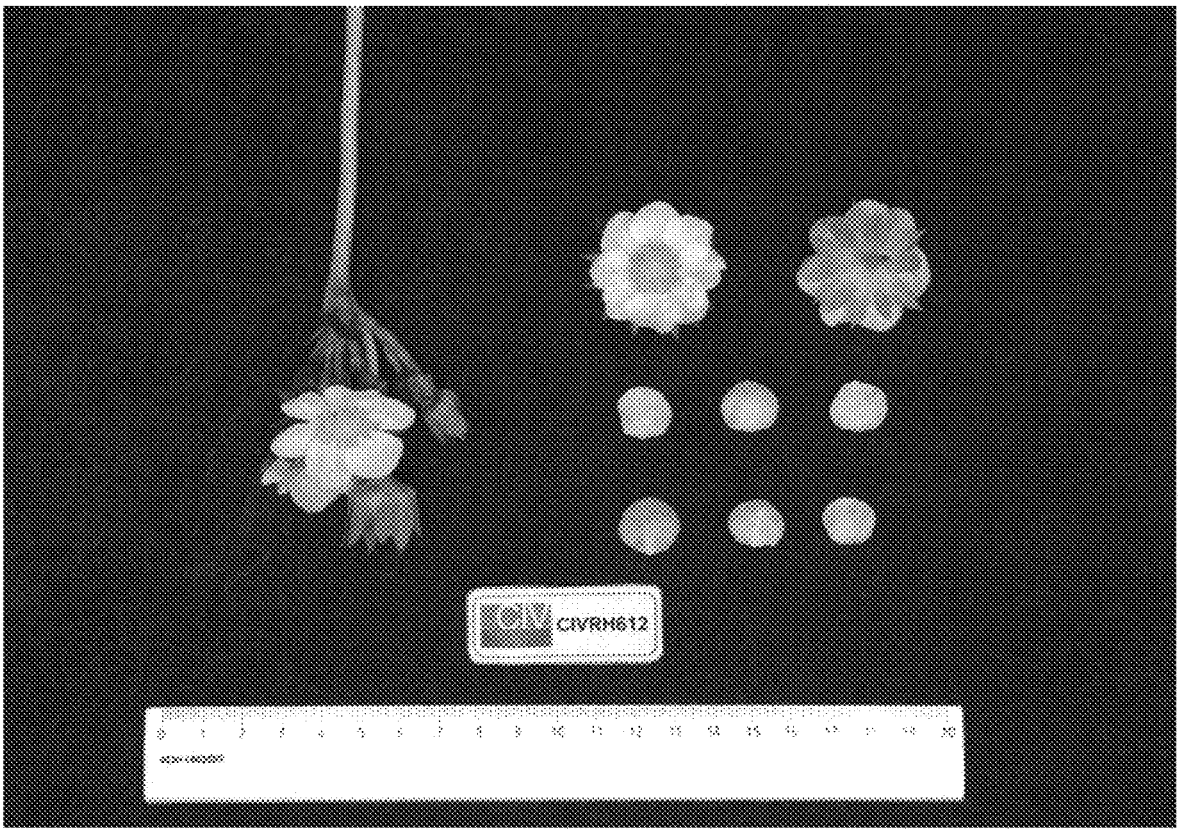
FIG. 2 shows typical flowers of 'CIVRH612'.
Figure 3:
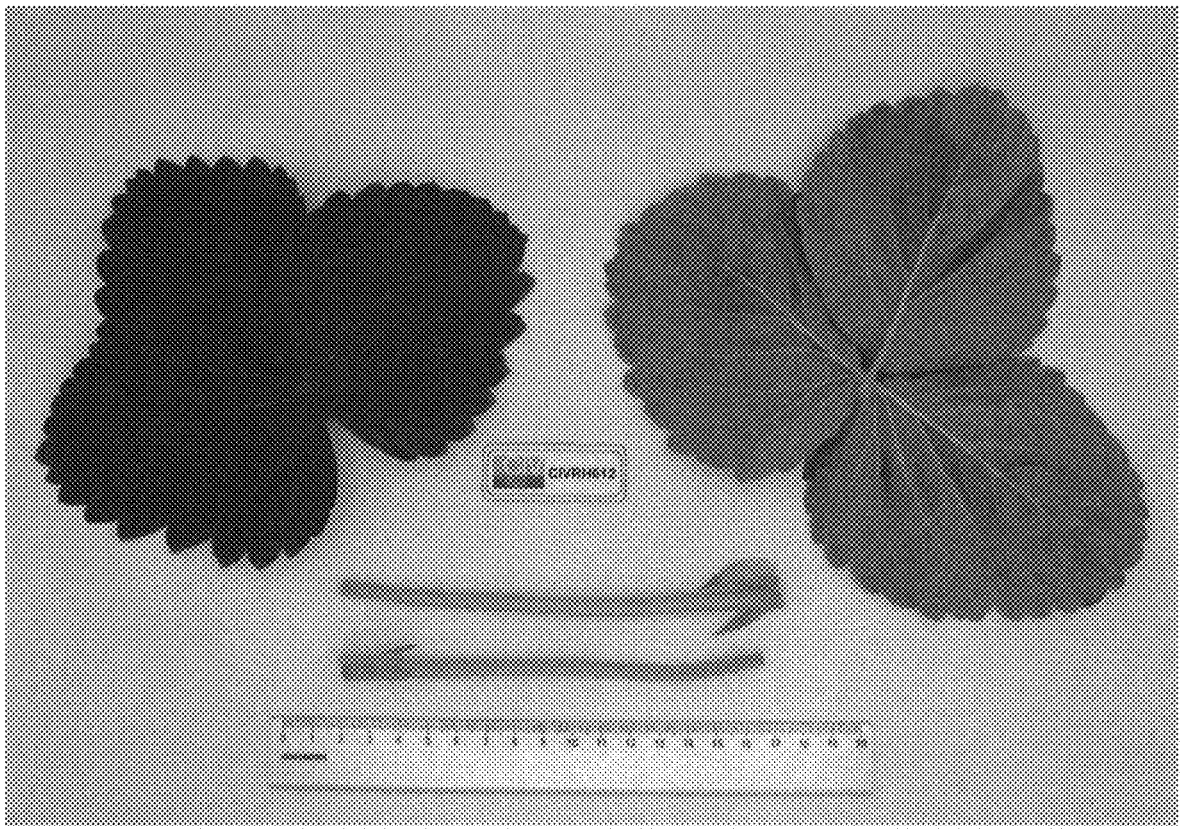
FIG. 3 shows typical leaves of 'CIVRH612'.
Figure 4:
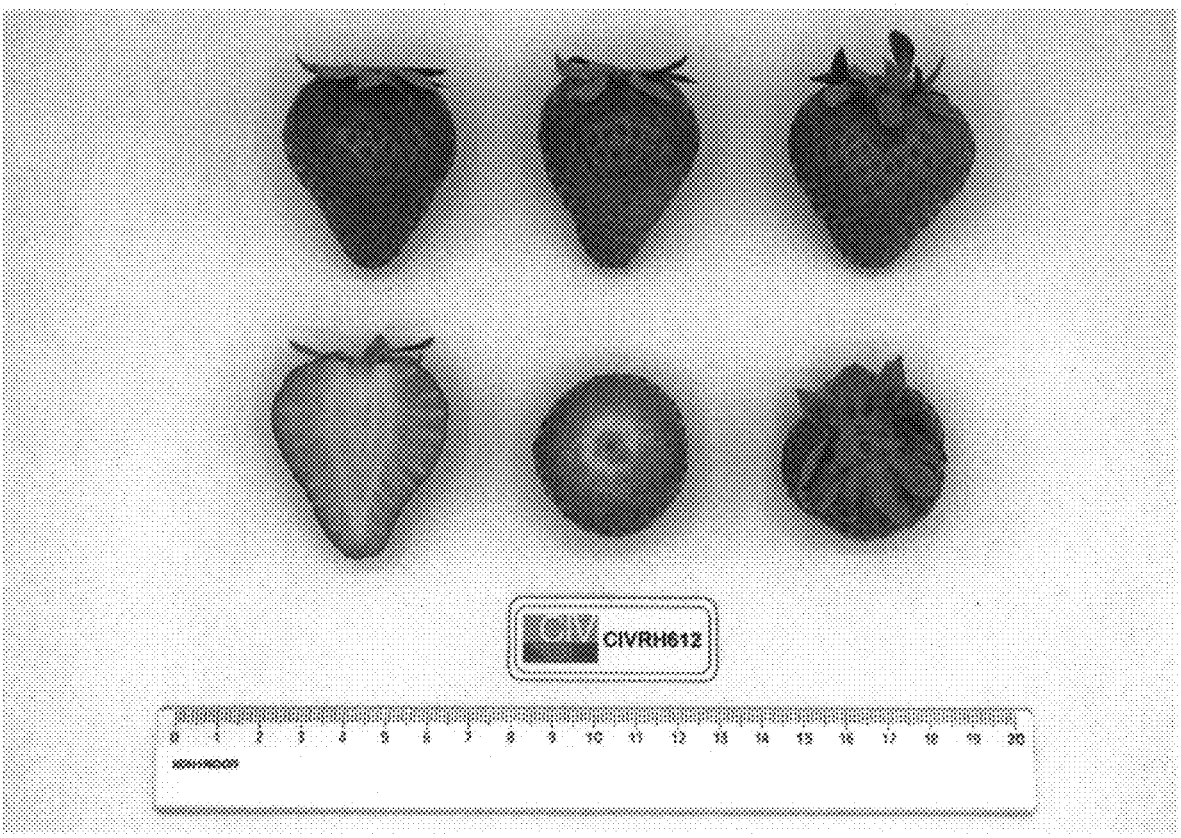
FIG. 4 shows typical fruits of 'CIVRH612'.

'CIVRH612' has not been observed under all possible environmental conditions. The characteristics of the new variety may vary in detail, depending upon variations in environmental factors, including weather (temperature, humidity and light intensity), day length, soil type and location.

The aforementioned photographs, together with the following observations, measurements and values describe the new strawberry variety 'CIVRH612', unless otherwise noted, taken during the 2018 growing season in San Giuseppe di Comacchio (Ferrara), Italy. The observations, measurements and values were taken from plants of 'CIVRH612' dug from a low-elevation nursery located in San Giuseppe di Comacchio (Ferrara), Italy, during 2018 and planted approximately 4 months later in San Giuseppe di Comacchio (Ferrara), Italy. Plants of the new strawberry variety 'CIVRH612' were grown under conditions which closely approximate those generally used in commercial practice.

Yield observations and fruit quality characteristics are averaged from 2 years of data collected from the 2017 through 2018 growing seasons. Flower measurements and characteristics are from secondary flowers unless otherwise noted. Fruit characteristics and measurements are from secondary fruit unless otherwise noted.

Color references are made to The Royal Horticultural Society Colour Chart (R.H.S.), 2001, except where general colors of ordinary significance are used. Color values were taken under daylight conditions at approximately 10:00 A.M. in San Giuseppe di Comacchio (Ferrara), Italy. The approximate age of the observed plants is 3 to 5 months.

The following tables 3-9 describe fruit, plant, stolon, foliage, fruiting truss, flower and pest/disease characteristics of the new strawberry 'CIVRH612'.

TABLE 3

FRUIT CHARACTERISTICS

| Characteristic | 'CIVRH612' |
|---|---|
| Color of mature fruit | Red (45A red group) |
| Color of internal flesh | Orange-red (33B orange-red group) |
| Length (cm) | Average 4.5 cm |
| Width (cm) | Average 4.9 cm |
| Ratio length/width | 1.16 |
| Calyx diameter (cm) | Average 3.5 cm |
| Average weight (gm) | Average 20 gm |
| Achene color | Yellow (150B yellow-green group) |
| Number of achenes per $cm^2$ | About 6.8 achenes/$cm^2$, measured in the middle of the fruit |
| Marketable yield (gm/pit) | Average 600-800 gm/plt |
| Size | Large |
| Predominant shape | Conical |
| Difference in shapes between primary and secondary fruit | Moderate |
| Band without achenes | Absent or very narrow |
| Unevenness of surface | Even or very slightly uneven |
| Evenness of color | Even or very slightly uneven |
| Glossiness | Strong |
| Insertion of achenes | Below the surface |
| Insertion of calyx | Level with the surface |
| Attitude of the calyx | Outward |
| Same size | |
| Size of calyx in relation to fruit diameter | |
| Adherence of calyx | Weak to medium |
| Firmness of skin | Firm |
| Firmness of flesh | Firm |
| Distribution of red color of the flesh | Marginal |
| Hollow center expression | Absent or small |
| Flavor | Very sweet, aromatic and juicy |
| Soluble solids (% brix) | 8.8° Brix |
| Time of first flowering | Early |
| Time of first harvesting | Early (first picking the 23rd of May 2019 in San Giuseppe di Comacchio (Ferrara), Italy) |
| Harvest period | From the end of May to October |
| Type of bearing | Day neutral |

TABLE 4

PLANT CHARACTERISTICS

| Characteristic | 'CIVRH612' |
|---|---|
| Height (cm) | Average 28 cm |
| Spread (cm) | Average 43 cm |
| Size | Medium to large |
| Habit | Upright |
| Density | Medium |
| Vigor | Medium |

TABLE 5

STOLON CHARACTERISTICS

| Characteristic | 'CIVRH612' |
|---|---|
| Average number per plant | About 25 stolons/mother plant in our nursery in San Giuseppe di Comacchio (Ferrara) Italy |
| Anthocyanin coloration | Absent |
| Anthocyanin intensity | None |
| Diameter at bract (mm) | Average 3.6 mm |
| Pubescence | Medium |

TABLE 6

| FOLIAGE CHARACTERISTICS | |
|---|---|
| Characteristic | 'CIVRH612' |
| Foliage: | |
| Color of upper surface | Green (141A green group) |
| Color of underside | Green (146B yellow-green group) |
| Shape in cross section | Concave |
| Interveinal blistering | Weak to medium |
| Glossiness | Medium |
| Number of leaflets | Three (3) |
| Terminal Leaflet: | |
| Length (cm) | Average 11.5 cm |
| Width (cm) | Average 11 cm |
| Length/width ratio | 1.04 |
| Serrations/leaf | Free |
| Size | Small to medium |
| Shape of base | Obtuse |
| Shape of teeth | Serrate to crenate |
| Petiole: | |
| Length (cm) | Average 15.9 cm |
| Diameter (mm) | Average 4.71 mm |
| Petiolule length (mm) | Average 8.8 mm |
| Pubescence | Weak |
| Attitude of hairs | Upwards |
| Stipule: | |
| Length (mm) | Average 28.7 mm |
| Width (mm) | Average 9.5 mm |
| Anthocyanin coloration | Absent or very weak |
| Color | Red-purple (63A red-purple group) |

TABLE 7

| FRUITING TRUSS CHARACTERISTICS | |
|---|---|
| Characteristic | 'CIVRH612' |
| Length (cm) | Average 25 cm |
| Position relative to foliage | Slight above to the foliage |
| Pubescence | Dense |
| Anthocyanin intensity | None |
| Attitude at first pick | Outward |

TABLE 8

| FLOWER CHARACTERISTICS | |
|---|---|
| Characteristic | 'CIVRH612' |
| Petal color | |
| Mature (upper) | White (155 D white group) |
| Mature (lower) | White (155 D white group) |
| Petal shape | |
| Overall | Rounded |
| Apex | Round |
| Base | Round |
| Petal length (mm) | Average 11.2 mm |
| Petal width (mm) | Average 12.2 mm |
| Petal length/width ratio | 0.92 |
| Number of petals/flower | About 5 to 6 |
| Sepals color | |
| Mature (upper) | Green (143 A green group) |
| Mature (lower) | Green (144 B yellow-green group) |
| Sepal shape | |
| Overall | |
| Apex | Pointed |
| Base | Broad |
| Sepal length (mm) | Average 8.8 mm |
| Sepal width (mm) | Average 4.8 mm |
| Sepal length/width ratio | 1.8 |
| Number of sepals/flower | About 10 to 12 |
| Corolla diameter (mm) | Average 33.5 mm |
| Calyx diameter (mm) | Average 34.2 mm |
| Size of calyx relative to corolla | Same size to slight bigger |
| Relative position of petals | Overlapping |

TABLE 9

| PEST AND DISEASE REACTIONS |
|---|
| 'CIVRH612' is a rustic plant quite tolerant to leaf and root diseases, and slightly susceptible to mildew. |

We claim:

1. A new and distinct strawberry plant named 'CIVRH612', as herein described and illustrated by the characteristics set forth above.

* * * * *